(12) United States Patent
Miyake et al.

(10) Patent No.: US 10,511,725 B2
(45) Date of Patent: Dec. 17, 2019

(54) IMAGE FORMING APPARATUS PROVIDED WITH SLIDABLE OPERATING PORTION

(71) Applicant: CANON KABUSHIKI KAISHA, Tokyo (JP)

(72) Inventors: Kazunori Miyake, Kashiwa (JP); Teruhiko Suzuki, Tokyo (JP); Masahiro Shinotsuka, Sashima-gun (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 15/728,913

(22) Filed: Oct. 10, 2017

(65) Prior Publication Data

US 2018/0103158 A1    Apr. 12, 2018

(30) Foreign Application Priority Data

Oct. 12, 2016   (JP) ................................. 2016-201170

(51) Int. Cl.
*H04N 1/00* (2006.01)
*G01N 29/275* (2006.01)

(52) U.S. Cl.
CPC ....... *H04N 1/00037* (2013.01); *G01N 29/275* (2013.01); *H04N 1/00082* (2013.01); *H04N 1/00559* (2013.01); *H04N 1/00915* (2013.01); *H04N 1/00408* (2013.01)

(58) Field of Classification Search
None
See application file for complete search history.

(56) References Cited

U.S. PATENT DOCUMENTS

| | | | |
|---|---|---|---|
| 2008/0175640 A1* | 7/2008 | Akiyama | ........... G03G 15/6552 399/405 |
| 2015/0261168 A1* | 9/2015 | Yokoyama | ............. G03G 15/80 399/81 |

FOREIGN PATENT DOCUMENTS

| | | |
|---|---|---|
| JP | 2013-070279 A | 4/2013 |
| JP | 2015-180973 A | 10/2015 |

* cited by examiner

*Primary Examiner* — Thomas D Lee
(74) *Attorney, Agent, or Firm* — Venable LLP

(57) ABSTRACT

An image forming apparatus includes a reader; an image former, provided below the reader, for forming an image on a sheet; a sheet discharge portion, provided between the reader and the image former, for discharging and stacking the sheet; an operating portion provided in a front side adjacent to the reader in the horizontal direction and slidable along a side of the reader; a sensor unit provided at a side of the reader in a outside of a slidable range of the operating portion, the sensor unit being can project a signal on the side of the reader and receiving a reflection wave of the signal to detect presence of the user in an area in the front side; and a controller for restoring a state of the apparatus from a sleeping state to a stand-by state in response to detection by the sensor unit.

20 Claims, 6 Drawing Sheets

IMAGE FORMING APPARATUS PROVIDED WITH SLIDABLE OPERATING PORTION

FIELD OF THE INVENTION AND RELATED ART

The present invention relates to an image forming apparatus equipped with a sensor for detecting the presence of a moving object such as a human body, with the use of a distance detection sensor such as an ultrasonic sensor, or the like.

There is disclosed in Japanese Laid-open Patent Application No. 2015-180973, an image forming apparatus equipped with a human detection sensor for changing an operational mode of an image forming apparatus from the sleep mode to the standby mode. Some of these human detection sensors are attached to the scanner portion of the image forming apparatus to improve the sensor in detection accuracy.

There is disclosed in Japanese Laid-open Patent Application No. 2013-70279, an image forming apparatus, the control panel of which is disposed on the front side of the main assembly of the apparatus, in such a manner that the control panel is next to the reading apparatus of the image forming apparatus, in terms of the horizontal direction. In the case of this image forming apparatus, the control panel is slidable in the direction which is parallel to the front side of the apparatus. Thus, a user is allowed to place the control panel in any position within a range in which the control panel is slidable. This structural arrangement, therefore, can improve the image forming apparatus in operability.

If the human sensor disclosed in Japanese Laid-open Patent Application No. 2015-180973 is applied to the image forming apparatus disclosed in Japanese Laid-open Patent Application No. 2013-70279, it is possible that the human sensor will be placed in a position in which it fails to detect the presence of a human.

SUMMARY OF THE INVENTION

The present invention was made in consideration of the above-described issue. Thus, the primary object of the present invention is to provide an image forming apparatus capable of accurately detecting the presence of a user in front of the apparatus, regardless of the positioning of the slidable control panel, when the user is approaching the apparatus to use the apparatus.

According to an aspect of the present invention, there is provided an image forming apparatus comprising a reader configured to read a original; an image forming portion provided below said reader with respect to a vertical direction and configured to form an image on a recording material; a sheet discharge portion provided between said reader and said image forming portion with respect to the vertical direction and configured to discharge and stack the recording material carrying the image formed by said image forming portion; an operating portion capable of being operated by a user and provided in a front side of said image forming apparatus and adjacent to said reader with respect to the horizontal direction, said operating portion being slidable along a side of said reader in the front side of said image forming apparatus; a sensor unit provided at the side of said reader in a outside of a slidable range of said operating portion, said sensor unit being capable of projecting a signal on the side of said reader and receiving a reflection wave of said signal to detect presence or absence of the user in an area in the front side of said image forming apparatus; and a controller configured to restore a state of said image forming apparatus from a sleeping state to a stand-by state in response to detection of the presence of the user in a detectable area, by said sensor unit.

Further features of the present invention will become apparent from the following description of exemplary embodiments with reference to the attached drawings.

BRIEF DESCRIPTION OF THE DRAWINGS

Part (a), part (b) and part (c) of FIG. 1 are a combination of a front and right side views of the image forming apparatus in one of the preferred embodiments of the present invention.

Part (a) and part (b) of FIG. 2 are top views of the image forming apparatus in the embodiment.

Figure 6:
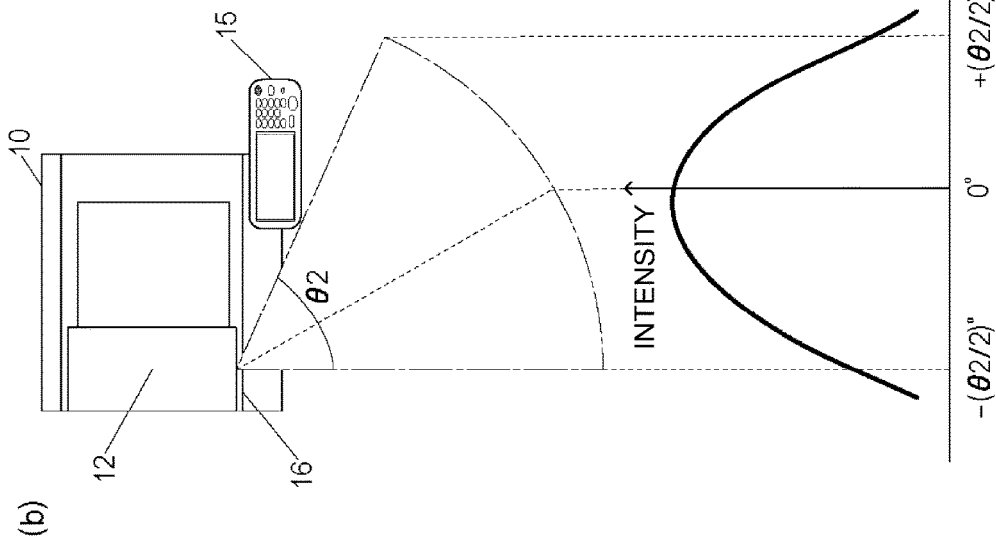
Figure 6:
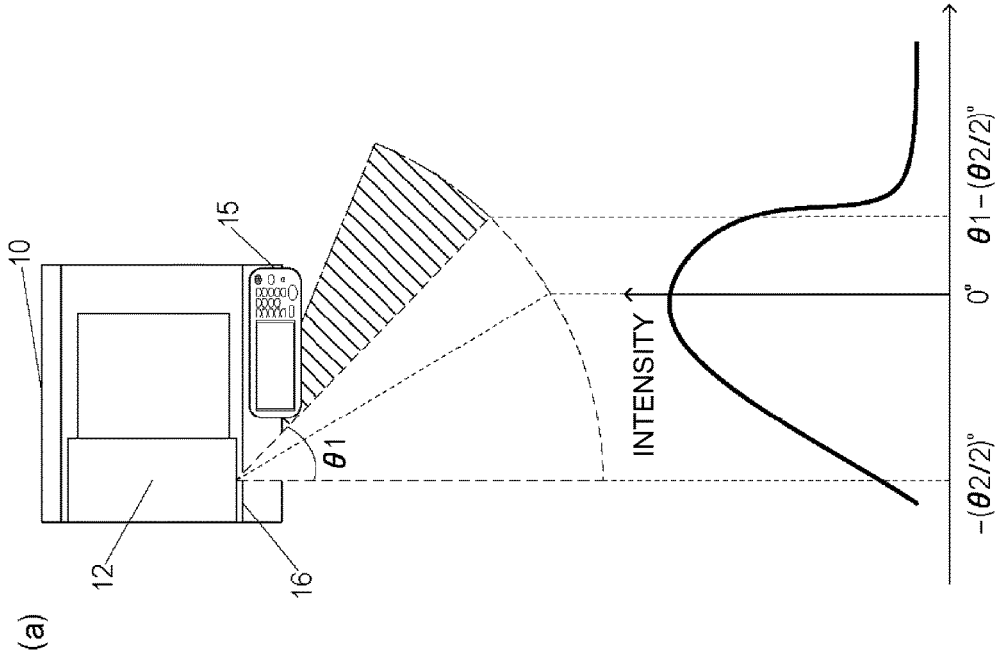

Part (a) and part (b) FIG. 6 are a schematic drawing which shows the positioning of the control panel, and the intensity of the ultrasonic waves which are emitted from the ultrasonic wave sensor unit.

DESCRIPTION OF THE EMBODIMENTS

Figure 1:
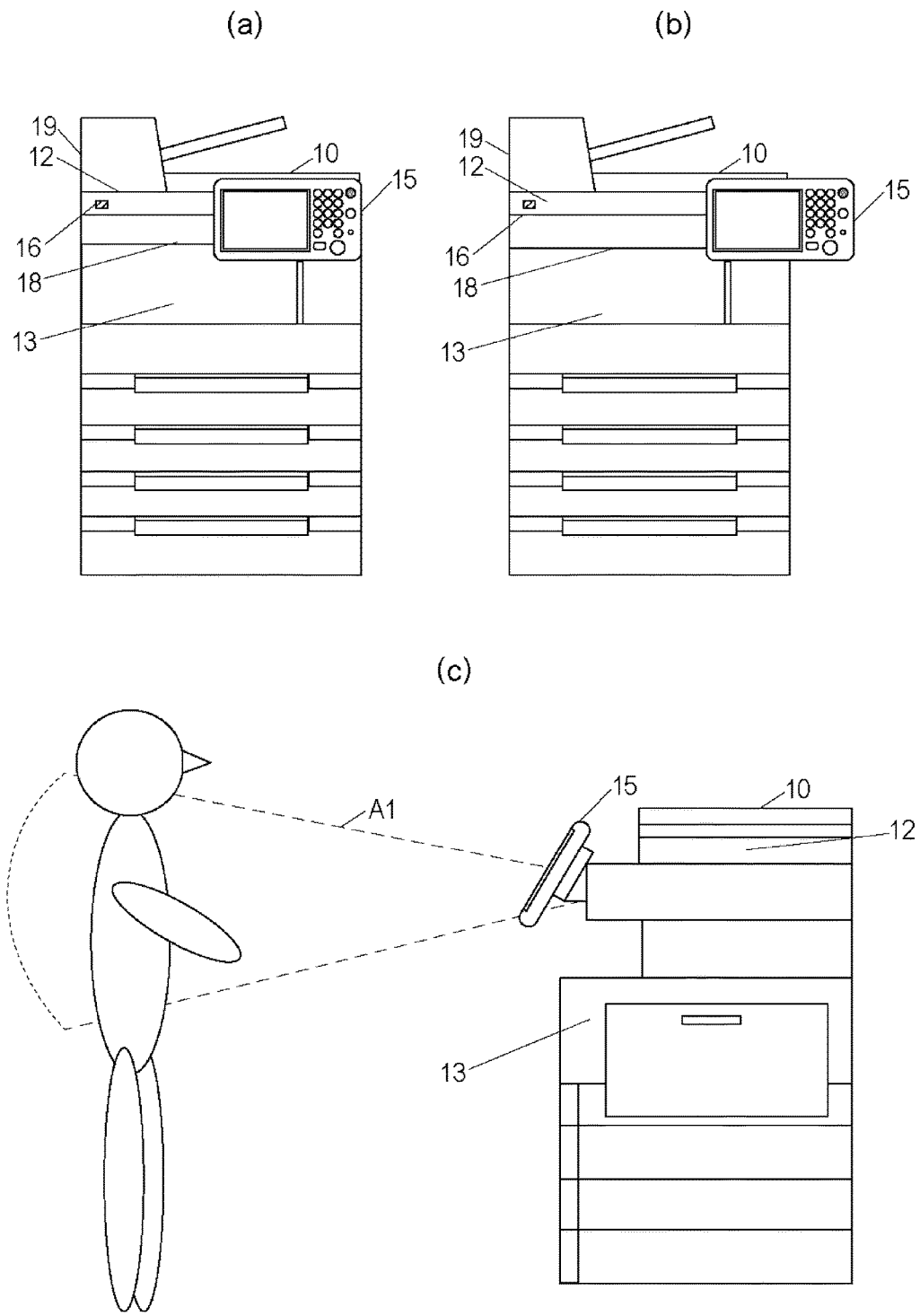

Part (a), part (b) and part (c) of FIG. 1 are a combination of the front and right side views of the image forming apparatus 10 in one of the preferred embodiments of the present invention.

The image forming apparatus 10 has multiple functions such as a printing function, a scanning function, a copying function, and a facsimile function. It has a printing portion 13, as an image forming portion, which forms an image on a sheet of recording medium. It has also an ultrasonic wave sensor unit 16 as a human sensor for detecting the presence of the user of the apparatus. The ultrasonic wave sensor unit 16 determines whether or not a user of the image forming apparatus 10 is in the area in which the user will be when the user operates the apparatus 10, by sending ultrasonic waves toward the area where the user will be to use the image forming apparatus 10, and catching the portion of the ultrasonic waves reflected by the user.

The image forming apparatus 10 has a control panel 15 which is usable by a user. It is structured so that the control panel 15 is slidable leftward or rightward. Part (a) of FIG. 1 shows the leftmost position to which the control panel 15 is slidable. Part (b) of FIG. 1 shows the rightmost position to which the control panel 15 is slidable. The control panel 15 comprises: a display portion, across which the state, or the like, of the image forming apparatus 10, is shown; and an inputting portion through which a user can input information into the image forming apparatus 10.

In the case of the image forming apparatus 10 in this embodiment, a delivery tray 18, into which sheets of recording medium are discharged in layers after the formation of an image on the sheets by a printing portion 13, is in the main assembly of the image forming apparatus 10. That is, the space into which the sheets of recording medium are discharged is in the main assembly of the image forming apparatus 10. Further, the image forming apparatus 10 in this embodiment is structured so that if a small sheet of recording medium is discharged while the control panel 15 is in the position shown in part (a) of FIG. 1, the discharged sheet of recording medium is hidden behind the control panel 15. That is, the image forming apparatus 10 in this embodiment is structured so that the line of sight between the sheets of recording medium in the delivery tray 18 and a user who is standing in front of the image forming apparatus 10 to pick up the sheets, is blocked by the control panel 15. Thus, it is difficult for a user to pick up the sheets of recording medium in the delivery tray 18 from the front side of the apparatus 10. That is, the image forming apparatus 10 is undesirable from the standpoint of the visibility of the sheets of recording medium in the delivery tray 18. In this embodiment, therefore, the image forming apparatus 10 is structured so that the control panel 15 is slidable into the position shown in part (a) of FIG. 1, or the position, shown in part (b) of FIG. 1, into which the control panel 15 is retractable from the position shown in part (a) of FIG. 1. With the control panel 15 being in the position shown in part (b) of FIG. 1, the apparatus 10 is better in terms of the visibility of the sheets of recording medium in the delivery tray 18, being therefore better in terms of the level of ease with which the sheets can be removed from the delivery tray 18.

On the other hand, if the control panel 15 is in the position shown in part (b) of FIG. 1, it protrudes from the right side of main assembly of the image forming apparatus 10. Thus, it is possible that the control panel 15 will interfere with a user when the user passes by the right side of the image forming apparatus 10. However, the control panel 15 is slidable back into the position shown in part (a) of FIG. 1, to prevent the control panel 15 from interfering with the user.

Since the image forming apparatus 10 in this embodiment is structured so that the control panel 15 is slidable as described above, it is possible to eliminate the demerit which the apparatus 10 suffers when the control panel 15 is in the position shown in part (a) of FIG. 1, and the demerit which the apparatus 10 suffers when the control panel 15 is in the position shown in part (b) of FIG. 1.

Next, positioning of the ultrasonic wave sensor unit 16 is described. In terms of the vertical direction, the ultrasonic wave sensor unit 16 is positioned so that it sends ultrasonic waves to the torso portion of a user, in order to ensure that the ultrasonic wave sensor unit 16 accurately detects the presence of a human. It is possible that a user will keep the cover of an automatic original feeding portion 19 open while the user uses the automatic original feeding portion 19. Thus, the automatic original feeding portion 19 is not a desirable location to attach the ultrasonic wave sensor unit 16. Further, in a case where the ultrasonic wave sensor unit 16 is disposed on the front side of the printing portion 13, it is possible that the ultrasonic wave sensor unit 16 will be attached to the front cover of the printing portion 13. It is also possible that the front cover will be provided with a slit and the ultrasonic wave sensor unit 16 will be disposed behind the front cover.

If the ultrasonic wave sensor unit 16 is attached to the front cover, it is possible that the front cover will increase in thickness, and therefore, the image forming apparatus 10 will increase in size. Further, if the ultrasonic wave sensor unit 16 is attached to the front cover, the ultrasonic wave sensor unit 16 is subjected to the impacts which occur as the front cover is opened or closed by a user to replenish the image forming portion with consumables, such as replacing a toner bottle or the like. Thus, vibration absorbing members or the like have to be added to the portion to which the ultrasonic wave sensor unit 16 is attached. Thus, it is possible for the image forming apparatus 10 to increase in cost.

If the front cover is provided with a slit, and the ultrasonic wave sensor unit 16 is disposed on the inward side of the front cover, the ultrasonic wave sensor unit 16 has to be positioned so that it does not interfere with the toner bottle, drum cartridge, and the like components. In other words, the image forming apparatus 10 has to be provided with an additional space to dispose the ultrasonic wave sensor unit 16, which possibly requires the image forming apparatus 10 to be increased in size.

This is why the ultrasonic wave sensor unit 16 in this embodiment is attached to the scanner portion 12 as an original reading portion. Thus, it is possible for the ultrasonic wave sensor unit 16 to accurately detect the presence of a user, without requiring the image forming apparatus 10 to be increased in size and cost.

Referring to part (c) of FIG. 1, which is a right side view of the image forming apparatus 10, the ultrasonic wave sensor unit 16 is attached to the scanner portion 12. It sends ultrasonic waves to the area sandwiched by dotted lines A1, that is, the torso portion of the user, so that the portion of the ultrasonic waves reflected by the user is received by the ultrasonic wave sensor unit 16.

Figure 2:
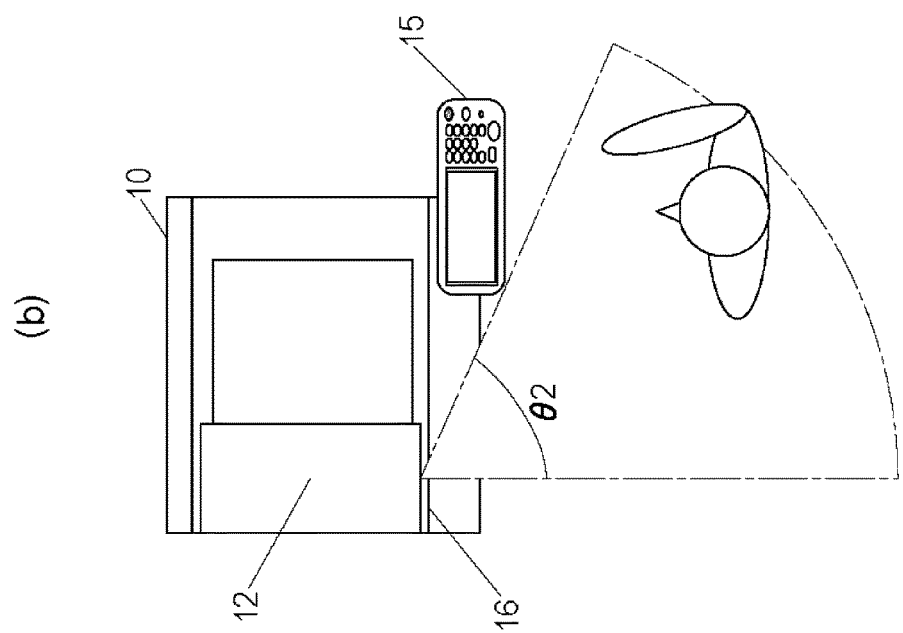
Figure 2:
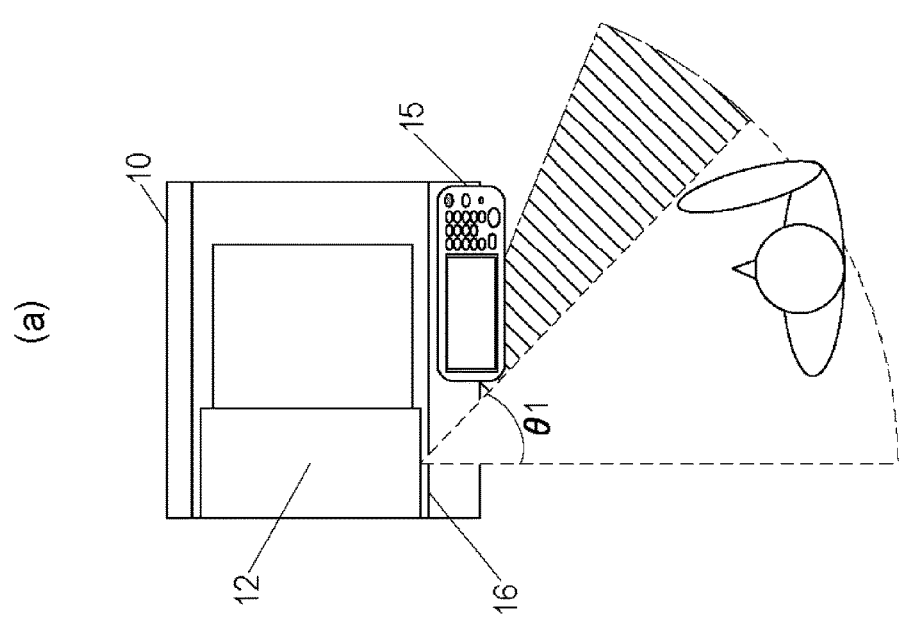

Part (a) and part (b) of FIG. 2 are top views of the image forming apparatus 10 according to the present invention. More specifically, parts (a) and (b) of FIG. 2 show the control panel 15 when the control panel 15 is in its leftmost and rightmost positions, respectively, into which the control panel 15 is slidable.

Referring to part (c) of FIG. 1 which shows a combination of an operator and the image forming apparatus 10 as seen from the direction (horizontal direction) in which the control panel 15 of the image forming apparatus 10 is slidable. In this embodiment, the ultrasonic waves are sent from the ultrasonic wave sensor 161 toward the area sandwiched by the dotted lines A1. When the operator is standing in the position shown in part (c) of FIG. 1, the control panel 15 is in the position in which the control panel 15 blocks the entirety of the area surrounded by the dotted lines A1. That is, the control panel 15 is in the position in which a part of the topmost portion of the control panel 15 protrudes above the area sandwiched by the dotted lines A1, and a part of the bottommost portion of the control panel 15 protrudes below the area sandwiched by the dotted lines A1.

In this embodiment, therefore, when the control panel 15 is in the position shown in part (a) of FIG. 1, a part of the control panel 15 is in the area, toward which the ultrasonic waves are outputted by the ultrasonic wave sensor 161. That is, in terms of the vertical direction of the image forming apparatus 10, the ultrasonic waves outputted by the ultrasonic wave sensor 161 toward the control panel 15 are entirely blocked by the control panel 15 (hatched area ($\theta_2-\theta_1$) in part (a) of FIG. 2. In other words, the ultrasonic wave sensor 161 is adjusted in the angle of its output waves so that the ultrasonic waves outputted toward the area hatched by diagonal lines (area (($\theta_2-\theta_1$) in part (a) of FIG. 2) do not pass the area above the control panel 15, and the area below the control panel 15, as shown in part (c) of FIG. 1.

Referring to FIG. 2, on the other hand, the ultrasonic waves (outputted toward the area in which a user will be when the user operates the image forming apparatus 10 (area $\theta_1$ in part (a) of FIG. 2, and area $\theta_2$ in part (b) of FIG. 2) is not blocked by the control panel 15. Therefore, it is possible to detect a user (presence of user) as the user approaches the control panel 15.

The ultrasonic wave sensor unit 16 is disposed so that the ultrasonic waves outputted by the ultrasonic wave sensor unit 16 cover only the area θ2. This angle of this area θ2 is set according to the attitude in which the ultrasonic wave sensor unit 16 is attached as shown in FIG. 3.

The ultrasonic waves outputted from the ultrasonic wave sensor unit 16 cannot go through the control panel 15. Thus, if the control panel 15 is in its leftmost position, shown in part (a) of FIG. 2, into which it is slidable, the area in which the ultrasonic wave sensor unit 16 can detect the presence of a user is area θ1. If the control panel 15 is in its rightmost position, shown in part (b) of FIG. 2, into which it is slidable, the area in which the ultrasonic wave sensor unit 16 can detect a user is area θ2.

Figure 3:
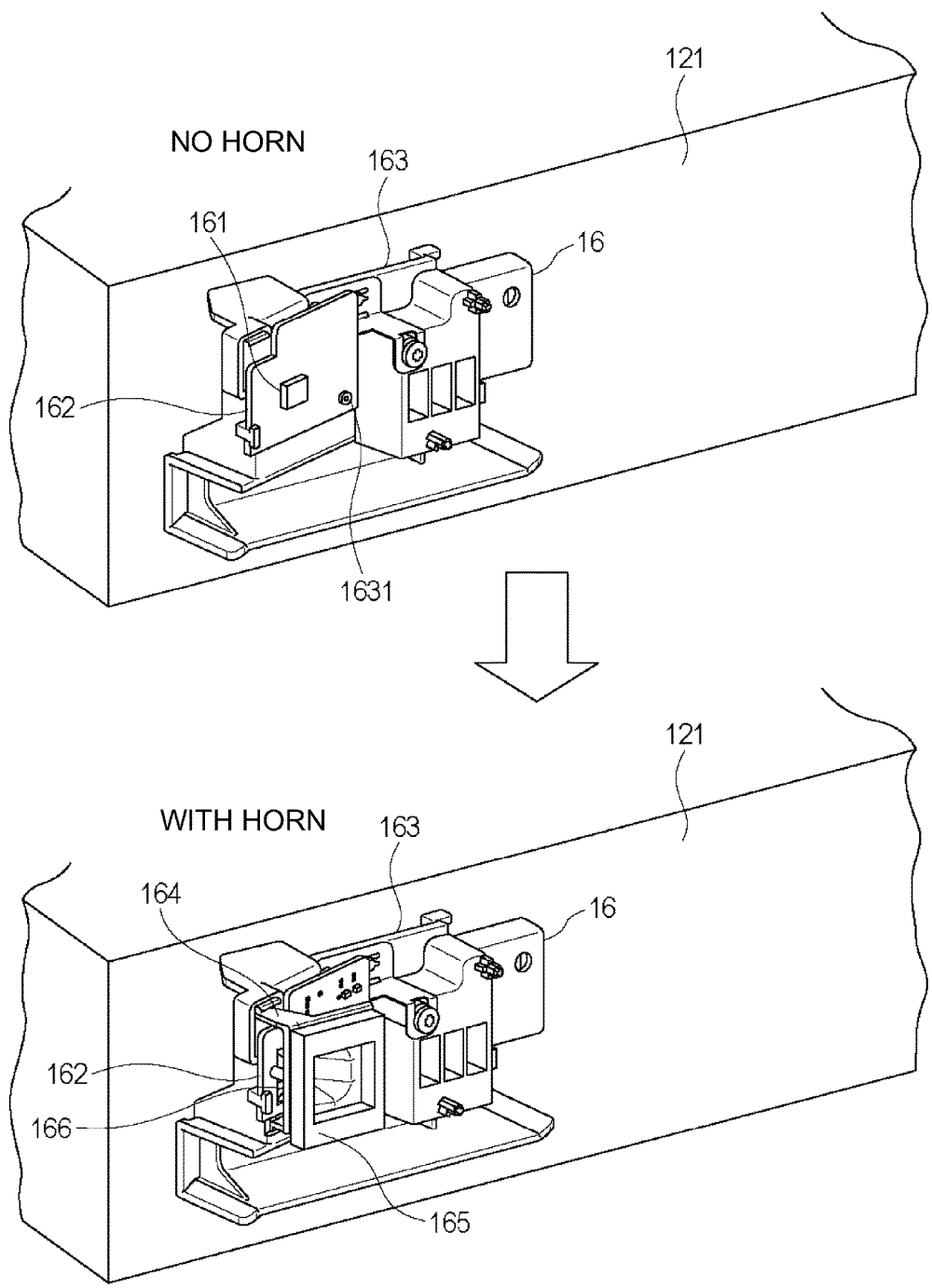
FIG. 3 is a combination of perspective views of the ultrasonic wave sensor unit before and after, respectively, the attachment of a horn to the sensor.

FIG. 3 is a combination of the drawings of the ultrasonic wave sensor unit 16 before and after, respectively, the ultrasonic wave sensor unit 16 is fitted with a horn.

The ultrasonic wave sensor unit 16 is fixed to the internal metallic frame 121 of the scanner portion 12. It comprises: a ultrasonic wave sensor 161; a substrate plate 162 to which the ultrasonic wave sensor 161 is attached; a seat 163 to which the substrate plate 162 is mounted; and a pair of cushioning members 165 and 166.

The ultrasonic wave sensor 161 is such a ultrasonic wave sensor that is capable of measuring the distance from itself to an object (moving object) in the adjacencies of the image forming apparatus 10, by outputting ultrasonic waves which are 40 kHz in frequency, that is, sonic waves which are inaudible to a human, and then, catching the portion of the outputted ultrasonic waves, which were reflected by the object. That is, not only does the ultrasonic wave sensor 161 function as a device that outputs ultrasonic waves which are 40 kHz in frequency, being therefore inaudible to a human, but also, as a device that catches the portions of the outputted ultrasonic waves that were reflected by the object. The ultrasonic wave sensor 161 is a SMD (surface mount device). That is, it is mounted on a surface of the substrate plate 162.

The substrate plate 162 is a laminar glass-epoxy plate having two layers. Not only does it support the ultrasonic wave sensor 161, but also, a driver 167 for driving the ultrasonic wave sensor 161 and an amplifier/comparator 168 for amplifying and digitizing the signals received by the ultrasonic wave sensor 161 (see FIG. 4).

The substrate plate 162 is fixed to the seat 163 with the use of small screws 1631. Further, the seat 163 is angled toward the control panel 15 so that the ultrasonic wave sensor 161 is aimed toward the control panel 15. Thus, not only is it possible for the ultrasonic wave sensor 161 to effectively detect a person (operator) as the person approaches the control panel 15, but also, it is possible to prevent the ultrasonic wave sensor 161 from detecting other persons than a user.

The horn 164 is for setting the directionality of the ultrasonic waves to be outputted from the ultrasonic wave sensor 161. Fitting the ultrasonic wave sensor 161 with the horn 164 increases the sensitivity of the ultrasonic wave sensor 161 and, therefore, makes the ultrasonic wave sensor 161 more stable in object detection. That is, it is a combination of the seat 163 and horn 164 that controls the area (in terms of angle) in which the ultrasonic wave sensor unit 16 can detect a user (see part (b) of FIG. 2).

The cushioning member 165 fills the gap between the horn 164 and the external cover of the scanner portion 12. Not only does it improve the ultrasonic wave sensor unit 16 in airtightness, but also, it prevents the ultrasonic waves (vibration) from being transmitted from the horn 164 to the external cover. The cushioning members 165 and 166 are desired to be made of such substances as Eptsealer (product of Nitto Denko Technologies Co., Ltd.) and Calmflex (product of Inoac Co., Ltd.) that is flexible, unlikely to transmit vibrations, and high in sound-proofing performance.

Figure 4:
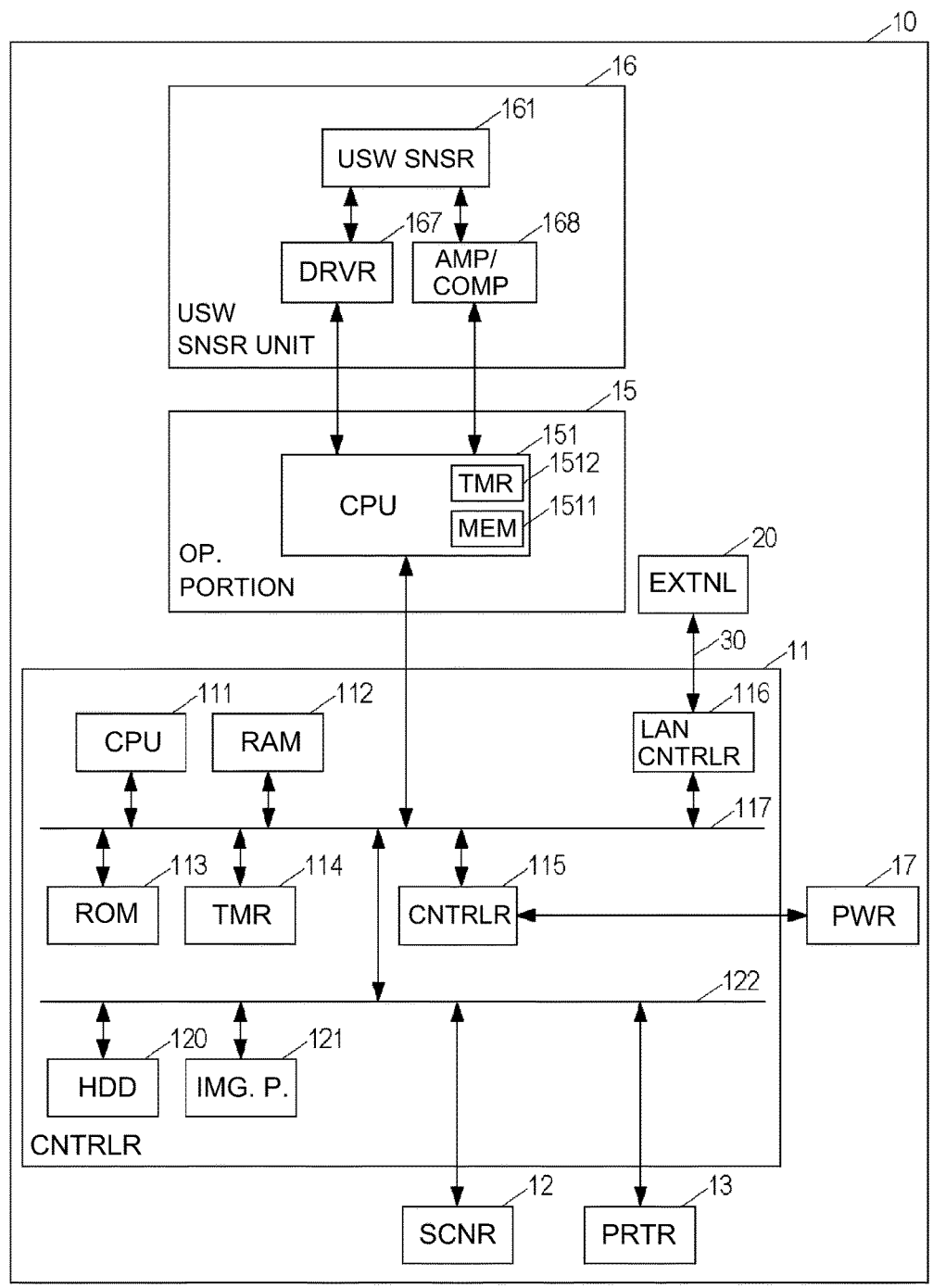
FIG. 4 is a block diagram of the image forming apparatus, which shows the configuration of the apparatus in terms of the positioning and connection of the hardware.

FIG. 4 is a block diagram of the image forming apparatus 10. It shows the hardware structure of the apparatus 10. The image forming apparatus 10 has: a controller 11 which controls the image forming apparatus 10 in operation; the scanner portion 12; the printing portion 13; the control panel 15; the ultrasonic wave sensor unit 16; and an electric power source 17.

The controller 11 can communicate with the scanner portion 12, printer portion 13, and control panel 15. It has a CPU 111, a RAM 112, a ROM 113, a timer 114, an electric power source controlling portion 115, and a LAN controller 116, which are connected to a system bus 117. Further, the controller 11 has a HDD 120 (hard disk drive) and an image processing portion 121, which are connected to the image bus 122.

The CPU 111 reads such programs as control programs stored in the ROM 113, and carries out the programs to control various devices in the image forming apparatus 10 in their operations. Further, it controls the various processes as the processes are carried out by the controller 11. Not only does the RAM 112 function as a system work memory for the operation of the CPU 111, but also, it is used for temporarily storing the image data. In the ROM 113, such data as boot program for the image forming apparatus 10 are stored. The timer 114 is a counter which can be cleared, start counting, stop counting, and confirm current count, following the programs carried out by the CPU 111.

The electric power source controlling portion 115 controls the electric power source of the image forming apparatus 10, in response to the instructions given by the CPU 111, and also, the instruction inputted by a user with the use of the control panel 15 (pressing (touching) of economy mode button, for example). The electric power source controlling portion 115 is capable of detecting whether or not the power source switch was turned off. If it detected that the power source switch was operated in the direction to turn off the electric power source, it sends to the CPU 111, the results of the detection as a power source turn-off demand. As the CPU 111 receives the power source turn-off command from the electric power source controlling portion 115, it puts the image forming apparatus 100 in a state in which the power source can be turned off, and instructs the power source controlling portion 115 to turn off the power source.

The LAN controller 116 communicates with an external apparatus 20 which is in connection to the LAN controller 116 through a network 30. In the HDD 120, various data such as system software and image data are stored. The image processing portion 121 reads the image data stored in the RAM 112, and carries out such processes as enlarging or reducing JPEG, JBIG, and the like, based on the read image data.

The scanner portion 12 generates image data by optically reading an original. It comprises: a driving portion for moving a reading head which reads an original; a driving portion for moving the original to where the original can be read by the head; etc.

The printing portion 13 forms an image on a sheet of recording medium with the use of an electrophotographic method. It comprises: a motor for rotating a photosensitive drum; a mechanical portion for applying pressure to a fixing device; a heater; etc.

The control panel 15 has: a CPU 151 which is in connection to the system bus 117; an input I/F, such as a LCD, a touch panel, hardware keys, a LED, etc., for a user, and outputs (displays) I/F for a user. Further, control panel 15 is in connection to the ultrasonic wave sensor unit 16.

The control portion CPU 151 is a single-chip microcomputer. It has internal memories 1511 such as RAM, ROM, and the like. It has also a timer 1512. By the way, the timer 1512 may be a software timer which is realized by one of the programs which are carried out by the control portion CPU 151.

Further, not only does the control portion CPU 151 control the LCD, touch panel, hardware keys, LED, etc., but also, the ultrasonic wave sensor unit 16. By the way, it is not mandatory that the ultrasonic wave sensor unit 16 is controlled by the control portion CPU 151. For example, the image forming apparatus 10 may be configured so that the ultrasonic wave sensor unit 16 is controlled by a CPU other than the control portion CPU 151.

The operations carried out by a user are detectable by the CPU 111 and control portion CPU 151 through the control panel 15, etc.

The image forming apparatus 10 in this embodiment can be put in one of two energy saving modes, that is, a standby mode and a sleep mode. The CPU 111 controls the image forming apparatus 10 in power consumption, by putting the image forming apparatus 10 in one of the two modes through the aforementioned power source controlling portion 115.

The standby mode (first mode) is such a mode that even when the image forming apparatus 10 is in this mode, a scanning operation can be started by the scanning portion, and a printing operation can be started by the printing portion 13. The sleep mode (second mode) is such a mode that when the image forming apparatus 10 is in this mode, the image forming apparatus 10 is smaller in the power consumption than in the standby mode. When the image forming apparatus 10 is switched in mode from the sleep mode to the standby mode, the power necessary to put the image forming apparatus 10 back in the standby mode is supplied to the devices which need to be activated to put the apparatus 10 back in the standby mode. The devices necessary to be reactivated are the LAN controller 116, power source controlling portion 115, ultrasonic wave sensor unit 16, and control portion CPU 151.

If the image forming apparatus 10 is not used for a preset length of time, the CPU 111 changes the image forming apparatus 10 in operational mode (power consumption mode) from the standby mode to the sleep mode. For example, if the control panel 15 is not used by a user for a preset length of time, and the image forming apparatus 10 does not receive a job from the external apparatus 20 for a preset length of time, the CPU 111 changes the image forming apparatus 10 in power consumption mode from the standby mode to the sleep mode.

The ultrasonic wave sensor unit 16 has the ultrasonic wave sensor 161, transmission driver 167, and amplifier/comparator 168. Further, it is in connection to the control portion CPU 151.

The control portion CPU 151 drives the ultrasonic wave sensor 161 through the transmission driver 167. The transmission driver 167 has a transmitting portion which converts the electrical signals given by the transmission driver 167, into vibrations (ultrasonic waves), and sends the ultrasonic waves frontward of the image forming apparatus 10. Further, the ultrasonic wave sensor 161 has such a receiving portion that as the ultrasonic waves are sent frontward of the image forming apparatus 10, from the transmitting portion, it catches the portions of the ultrasonic waves, which were reflected by an object.

The amplifier/comparator 168 amplifies and digitizes the electrical signals given by the ultrasonic wave sensor 161 so that the electrical signals can be processed by the control portion CPU 151. The control portion CPU 151 can receive the output signals from the amplifier/comparator as they arrive.

The ultrasonic wave sensor 161 in this embodiment is used as both a transmitter and receiver. However, it is not mandatory that the ultrasonic wave sensor 161 is used as both the transmitter and receiver. For example, the image forming apparatus 10 may be provided with an ultrasonic wave transmitter, and a ultrasonic wave receiver which is independent from the ultrasonic wave transmitter, and be configured so that transmitter and receiver are connected to the transmission driver 167 and amplifier/comparator 168, respectively.

Since the image forming apparatus 10 is configured as described above, as a person (user) approaches the image forming apparatus 10 while the apparatus 10 is in the sleep mode, the person (user) is detected by the ultrasonic wave sensor unit 16, and therefore, the apparatus 10 is automatically changed in operational mode from the sleep mode to the standby mode.

Figure 5:
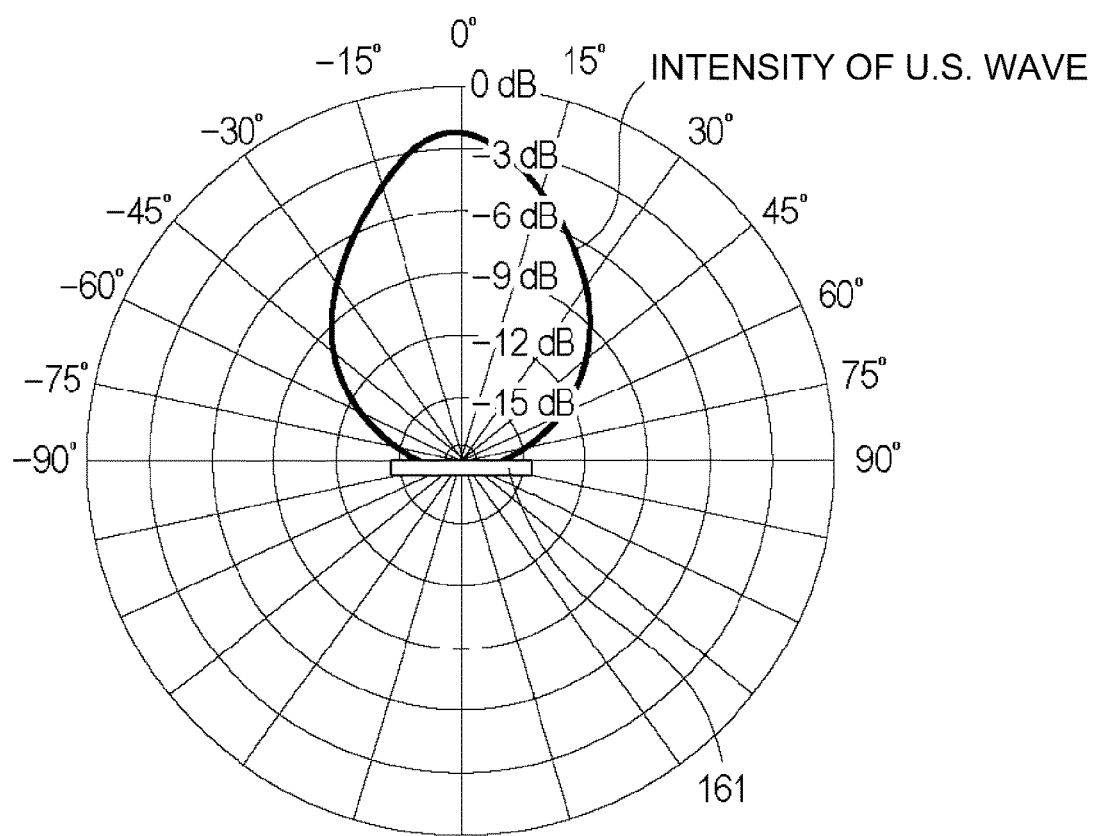
FIG. 5 is a schematic drawing which shows the range of the ultrasonic wave sensor, and the intensity of the ultrasonic wave.

FIG. 5 shows the relationship between the area to which ultrasonic waves are sent from the ultrasonic wave sensor unit 16 and the intensity of the waves. The ultrasonic wave sensor 161 is on a flat plane which coincides with a line 90°-90° in FIG. 5. Thus, fitting the ultrasonic wave sensor unit 16 with the horn 164 shown in FIG. 3 makes it possible to prevent the ultrasonic waves from undesirably widely dispersing. Thus, it makes it possible to control the ultrasonic wave sensor unit 16 in directionality so that the direction (0°), which is perpendicular to the surface on which the ultrasonic wave sensor unit 16 is, becomes the highest in intensity of the ultrasonic waves.

Part (a) and part (b) of FIG. 6 show the relationship between a given point in the area toward which ultrasonic waves are set by the ultrasonic wave sensor unit 16, and the intensity of the ultrasonic waves at the given point. Part (a) and (b) of FIG. 6 show the relationship when the control panel 15 is in the leftmost and rightmost positions, respectively, to which the control panel 15 is slidable. The ultrasonic wave sensor unit 16 is disposed so that the center line of the area θ2, shown in part (b) of FIG. 6, becomes parallel to the vertical direction)) (0°) of the ultrasonic wave sensor 161.

As the control panel 15 is in the leftmost position shown in part (a) of FIG. 6) into which the control panel 15 is slidable, the ultrasonic wave sensor unit 16 sends ultrasonic waves into the area between an angle −(θ2/2°) and an angle 0°, in various intensities shown in FIG. 5. In this case, the ultrasonic waves are highest (strongest) at angle 0°. In the area between angle 0° to angle ((θ1−(θ2/2)°), the intensity of the ultrasonic waves is proportional to the values shown in FIG. 5. However, the area beyond angle (θ1−(θ2/2)) is substantially less in the intensity of the ultrasonic waves, because the ultrasonic waves sent toward this area are blocked by the control panel 15. Thus, the area, in which a user of the image forming apparatus 10 can be accurately detected by the ultrasonic wave sensor unit 16 as the user approaches the control panel 15 when the control panel 15 is in the leftmost position is, area θ1. That is, by setting the ultrasonic wave sensor unit 16 so that it outputs ultrasonic waves only toward the area θ1, it is possible to accurately detect a user as the user approaches the control panel 15.

On the other hand, when the control panel 15 is in its rightmost position shown in part (b) of FIG. 6, the ultrasonic waves which are outputted by the ultrasonic wave sensor unit 16 are strongest at angle 0°, and the intensity of the ultrasonic waves at a given point in an area between angle −(θ2/2°) and angle +(θ2/2°) is as shown in FIG. 5. Thus, the area in which the ultrasonic wave sensor unit 16 can detect a user as the user approaches to use the image forming apparatus 10 is the area θ2. Therefore, the ultrasonic wave sensor unit 16 can detect a user as the user approaches the control panel 15 when the control panel 15 is in its rightmost position.

As described above, the ultrasonic wave sensor unit 16 is attached to the scanner portion 12 so that the ultrasonic waves from the ultrasonic wave sensor unit 16 covers the area θ2. Thus, the ultrasonic wave sensor unit 16 can accurately detect a user, regardless of the position of the control panel 15, as the user approaches the control panel 15 to use the image forming apparatus 10.

In this embodiment, the ultrasonic wave sensor unit 16 is set so that the ultrasonic waves from the ultrasonic wave sensor unit 16 cover area θ2. However, it may be set so that it covers an area which is wider than area θ2. The effects of such a setting are the same as those obtainable when it is set as described above.

Further, in this embodiment, the image forming apparatus 10 is structured so that the ultrasonic wave sensor unit 16 is changed in its detection area in which it can detect a user, by the positioning of the control panel 15. However, the image forming apparatus 10 may be structured so that the ultrasonic wave sensor unit 16 can be changed in its detection area, by changing the unit 16 in the angle of its ultrasonic wave output, according to the position of the control panel 15.

At this time, an example of the method for determining the area which is covered by the ultrasonic wave sensor unit 16 is described. Here, the area in which a user is detected can be clarified by finding the area which causes the image forming apparatus 10 to change in operational mode from the sleep mode to the standby mode.

First, a reflective plate having a preset size (10 mm×1000 mm) is positioned a preset distance away from the ultrasonic wave sensor unit 16. Then, in order to obtain the precise distance of the reflective plate from the ultrasonic wave sensor unit 16, at which the ultrasonic wave sensor unit 16 detects the reflective plate (object), the distance between this reflective plate and the ultrasonic wave sensor unit 16 is reduced in steps by a preset amount (50 mm, for example), while detecting the position of the reflective plate (distance between reflective plate and ultrasonic wave sensor unit 16), in which the image forming apparatus 10 changes in operational mode from the sleep mode to the standby mode. During this step, the reflective plate is directed so that the normal line of the reflective plate always squarely faces the ultrasonic wave transmitting portion of the ultrasonic wave sensor unit 16.

Next, the position in which a user is when the image forming apparatus 10 is changed in operational mode from the sleep mode to the standby mode is detected. By going through these steps, it is possible to clarify the horizontal range of detection of the ultrasonic wave sensor unit 16. Further, the vertical range of detection of the ultrasonic wave sensor unit 16 can be precisely detected by vertically moving the reflective plate (of preset size) within the range in which the reflective plate is detectible. By using a reflective plate of a preset size as described above, it is possible to clarify the detection area of the ultrasonic wave sensor unit 16.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-201170 filed on Oct. 12, 2016, which is hereby incorporated by reference herein in its entirety.

What is claimed is:

1. An image forming apparatus comprising:
   a reader configured to read an original;
   an image forming portion provided below said reader with respect to a vertical direction and configured to form an image on a recording material;
   a sheet discharge portion provided between said reader and said image forming portion with respect to the vertical direction and configured to discharge and stack the recording material carrying the image formed by said image forming portion;
   an operating portion capable of being operated by a user and provided on a front side of said image forming apparatus and adjacent to said reader with respect to a horizontal direction, said operating portion being slidable along a portion of a side of said reader on the front side of said image forming apparatus; and
   a sensor unit provided on the side of said reader on which said operating portion slides, said sensor unit being outside of a slidable range of said operating portion with respect to a direction of a sliding movement and being disposed closer to a back side of said image forming apparatus than said operation portion with respect to a front and rear direction of said image forming apparatus, said sensor unit being capable of detecting a user in the adjacencies of said image forming apparatus.

2. An apparatus according to claim 1, wherein said sensor unit is capable of (i) projecting a signal toward an area in the front side of said image forming apparatus and (ii) receiving a reflection wave of the signal to detect presence or absence of the user in the area, and
   wherein said sensor unit is disposed such that a detectable area of said sensor unit covers a part of a movement path of said operating portion, and said operating portion blocks, when said operating portion is at a position closest to said sensor unit within the slidable range of said operating portion, no part of an angle range of projection of the signal of said sensor unit.

3. An apparatus according to claim 2, wherein said sensor unit is disposed on a side of said reader on the front side of said image forming apparatus such that a maximum intensity of an intensity distribution of an output wave of the signal is at a side of said image forming apparatus at which said operating portion is provided with respect to the front and rear direction of said image forming apparatus.

4. An apparatus according to claim 3, wherein said sensor unit is provided such that the maximum intensity is not blocked irrespective of the position of said operating portion in the direction of sliding movement.

5. An apparatus according to claim 2, wherein said sensor unit includes a sensor provided with an output portion configured to output the signal and a reception portion configured to receive the reflection wave and also includes a horn configured to provide a directivity property for the signal by limiting an angle of a range of the projection of the signal.

6. An apparatus according to claim 1, wherein the recording material stacked in said sheet discharge portion can be taken out at a position below said operating portion taking a position closest to said sensor unit with respect to the direction of the sliding movement, and wherein with respect to the direction of the sliding movement, an overlapping length between said operating portion taking the position closest to said sensor unit and said sheet discharge portion is longer than an overlapping length between said operating portion taking a position most remote from said sensor unit and said sheet discharge portion.

7. An apparatus according to claim 6, wherein when said operating portion takes the position most remote from said sensor unit, an end portion, remote from said sensor unit, of said operating portion projects beyond an end surface of said image forming apparatus in the direction of the sliding movement.

8. An apparatus according to claim 1, wherein said sensor unit is disposed such that said sensor unit is between an upper end and a lower end of said operating portion with respect to the vertical direction.

9. An apparatus according to claim 1, further comprising a controller configured to restore a state of said image forming apparatus from a sleeping state to a stand-by state in response to detection of the presence of the user in the area by said sensor unit.

10. An apparatus according to claim 1, wherein said reader includes an external cover forming an external appearance and a metallic frame provided inside said external cover, and said sensor unit is fixed to said metallic frame.

11. An image forming apparatus comprising:
a reader configured to read an original and provided with a sensor unit being capable of detecting a user in the adjacencies of said image forming apparatus;
an image forming portion provided below said reader with respect to a vertical direction and configured to form an image on a recording material;
a sheet discharge portion provided between said reader and said image forming portion with respect to the vertical direction and configured to discharge and stack the recording material carrying the image formed by said image forming portion; and
an operating portion capable of being operated by the user and provided on the front side of said image forming apparatus and adjacent to said reader with respect to a horizontal direction, said operating portion being slidable along the side of said reader on the front side of said image forming apparatus,
wherein said sensor unit is provided on said reader outside of a slidable range of said operating portion and is disposed closer to a back side of said image forming apparatus than said operation portion with respect to a front and rear direction of said image forming apparatus.

12. An apparatus according to claim 11, wherein said sensor unit is capable of (i) projecting a signal toward an area on a front side of said image forming apparatus from a side of said reader on the front side of said image forming apparatus, and (ii) receiving a reflection wave of the signal to detect presence or absence of a user in the area, and
wherein said sensor unit is disposed such that a detectable area of said sensor unit covers a part of a movement path of said operating portion, and said operating portion blocks, when said operating portion is at a position closest to said sensor unit within the slidable range of said operating portion, no part of an angle range of projection of the signal of said sensor unit.

13. An apparatus according to claim 12, wherein said sensor unit is disposed on a side of said reader on the front side of said image forming apparatus such that a maximum intensity of an intensity distribution of an output wave of the signal is at a side of said image forming apparatus at which said operating portion is provided with respect to a front and rear direction of said image forming apparatus.

14. An apparatus according to claim 13, wherein said sensor unit is provided such that the maximum intensity is not blocked irrespective of the position of said operating portion in the direction of sliding movement.

15. An apparatus according to claim 12, wherein said sensor unit includes a sensor provided with an output portion configured to output the signal and a reception portion configured to receive the reflection wave and also includes a horn configured to provide a directivity property for the signal by limiting an angle of a range of the projection of the signal.

16. An apparatus according to claim 11, wherein the recording material stacked in said sheet discharge portion can be taken out at a position below said operating portion taking a position closest to said sensor unit with respect to a direction of the sliding movement, and wherein with respect to the direction of the sliding movement, an overlapping length between said operating portion taking the position closest to said sensor unit and said sheet discharge portion is longer than an overlapping length between said operating portion taking a position most remote from said sensor unit and said sheet discharge portion.

17. An apparatus according to claim 16, wherein when said operating portion takes the position most remote from said sensor unit, an end portion, remote from said sensor unit, of said operating portion projects beyond an end surface of said image forming apparatus in the direction of the sliding movement.

18. An apparatus according to claim 11, wherein said sensor unit is disposed such that said sensor unit is between an upper end and a lower end of said operating portion with respect to the vertical direction.

19. An apparatus according to claim 11, further comprising a controller configured to restore a state of said image forming apparatus from a sleeping state to a stand-by state in response to detection of the presence of the user in the area by said sensor unit.

20. An apparatus according to claim 11, wherein said sensor unit is disposed on a side of said reader on the front side of said image forming apparatus.

* * * * *